United States Patent [19]

Zaugg et al.

[11] 4,137,232
[45] Jan. 30, 1979

[54] 2,8-DISUBSTITUTED-10-HYDROXY-5,5-DIMETHYL-1,2,3,4-TETRAHYDRO-5H-[1]BENZOPYRANO[4,3-c]PYRIDINE

[75] Inventors: Harold E. Zaugg, Lake Forest; Cheuk M. Lee, Libertyville, both of Ill.

[73] Assignee: Abbott Laboratories, North Chicago, Ill.

[21] Appl. No.: 897,620

[22] Filed: Apr. 19, 1978

[51] Int. Cl.$^2$ .......................................... C07D 491/04
[52] U.S. Cl. ...................................... 546/89; 424/263
[58] Field of Search ............ 260/295 T, 296 T, 297 T

[56] References Cited

U.S. PATENT DOCUMENTS

| | | | |
|---|---|---|---|
| 3,429,889 | 2/1969 | Shulgin | 260/295 T |
| 3,915,996 | 10/1975 | Wright et al. | 260/345.3 |
| 3,932,432 | 1/1976 | Winn | 260/297 T |
| 4,081,449 | 3/1978 | Winn | 260/293.58 |

FOREIGN PATENT DOCUMENTS 1165025 9/1969 United Kingdom ................ 260/297 T Primary Examiner—John D. Randolph
Attorney, Agent, or Firm—Robert L. Niblack; Gildo E. Fato

[57] ABSTRACT

A compound of the formula

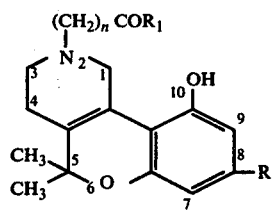

wherein n is 1 or 2; R is $C_3$–$C_{20}$ alkyl, phenyl alkyl or substituted phenyl alkyl; $R_1$ is $NR_2R_3$ where $R_2$ and $R_3$ each are H, loweralkyl or phenyl or substituted phenyl.

The compounds of this invention are useful as tranquilizers, analgesics, and sedative-hypnotics.

9 Claims, No Drawings

2,8-DISUBSTITUTED-10-HYDROXY-5,5-DIMETHYL-1,2,3,4-TETRAHYDRO-5H-[1]BENZOPYRANO[4,3-c]PYRIDINE

SUMMARY OF THE INVENTION

The present invention relates to Benzopyrans and more particularly to 2,8-disubstituted-10-hydroxy-5,5-dimethyl-1,2,3,4-tetrahydro-5H-[1]benzopyrano[4,3-c]-pyridines which are useful as tranquilizers, analgesics, and sedative-hypnotics.

The compounds may be prepared by alkylation of 10-hydroxy-5,5-dimethyl-8-substituted-1,2,3,4-tetrahydro-5H-[1]benzopyrano[4,3-c]pyridine with haloacetamides, halopropionamides and alkyl haloacetates with an acid acceptor such as triethylamine in dimethylformide.

DETAILED DESCRIPTION OF THE INVENTION

This invention relates to Benzopyrano [4,3-c]pyridine-2-acetamides which are useful as tranquilizers, analgesics and sedative-hypnotics. The compounds of this invention are represented by the formula

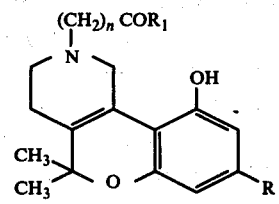

n is 1 or 2;
R is $C_3$–$C_{20}$ straight or branched alkyl or araylalkyl; and
$R_1$ is $NR_2R_3$ where $R_2$ and $R_3$ each are H, lower alkyl, phenyl or substituted phenyl, namely halophenyl such as chloro, bromo or fluorophenyl.

The term "$C_3$–$C_{20}$ alkyl" as used herein refers to both straight and branched chain alkyl radicals, including n-propyl, iso-propyl, n-butyl, 2-tetradecyl, 2-eicosanyl, and the like.

The term "phenylalkyl" refers to the straight or branched alkyl group of 1 to 10 carbon atoms where one of the hydrogen atoms of the alkyl group is substituted by phenyl or a substituted phenyl, namely halophenyl such as chloro, bromo or fluorophenyl, or loweralkyl phenyl.

The term "loweralkyl", as used herein, refers to $C_1$–$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The compounds of this invention exhibit activity as analgesics, tranquilizers, and sedative-hypnotics. The activity of analgesia is obtained in dosages from 20 to 40 mg/kg. of body weight orally and from 10 to 20 mg/kg. body-weight interperitoneally (i.p.). The analgesic activity was first established using the rat tail flick method of Harris, et al., J.P.E.T. 169, 17 (1969) and the hot plate analgesia test, and confirmed in the mouse writhing test.

The compounds exhibit mild tranquilizing activity in mice at dosages of from 5 to 40 mg/kg. intraperitoneally and in dogs at dosages of from 1 to 5 mg/kg. orally. If tranquilization is desired during the day, lower dosages are administered. If the higher dosages are administered, the compounds are useful as sedative-hypnotics and can be employed to induce sleep.

The present compounds may generally be prepared as illustrated by Scheme I:

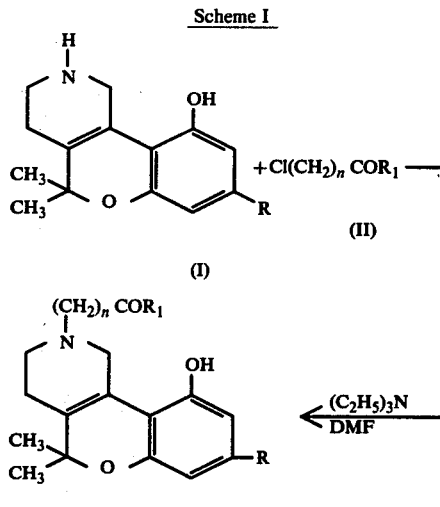

where n and $R_1$ are as defined above and R is

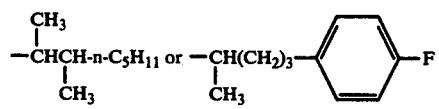

According to the process illustrated in Scheme I, the present compounds can be prepared by the alkylation of 10-hydroxy-5,5-dimethyl-8-substituted-1,2,3,4-tetrahydro-5H-[1]benzopyrano[4,3-c]pyridine with an haloacetamide, halopropionamide, or alkyl haloacetate in the presence of an acid acceptor such as triethylamine in dimethylformide (DMF) at room temperature.

The starting material (Compound I) may be Compound (I-a): 10-hydroxy-5,5-dimethyl-8-(1,2-dimethyl-heptyl)-1,2,3,4-tetrahydro-5H-[1]benzopyrano[4,3-c]pyridine; Compound (I-b): 8-[5-(4-fluorophenyl)-2-pentyl]-10-hydroxy-5,5-dimethyl-1,2,3,4-tetrahydro-5H-[1]benzopyrano[4,3-c]pyridine; or Compound (I-c): 10-hydroxy-8-isopropyl-5,5-dimethyl-1,2,3,4-tetrahydro-5H-[1]benzopyrano[4,3-c]pyridine. The starting materials, i.e., compounds, are represented by the formula:

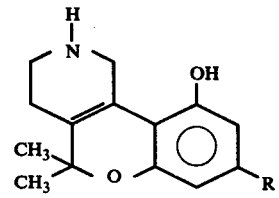

wherein:

Compound I-a: R = $-\overset{\underset{\displaystyle CH_3}{|}}{\underset{\underset{\displaystyle CH_3}{|}}{C}}H\text{-n-}C_5H_{11}$; and Compound I-b: R = 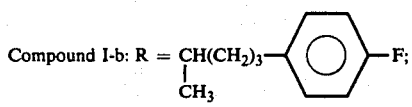

and Compound I-c: R = CH(CH₃)₂.

The compounds that may be produced according to the present invention include:

I. 10-Hydroxy-5,5-dimethyl-8-(1,2-dimethylheptyl)-1,2,3,4-tetrahydro-5H-[1]benzopyrano 4,3-c pyridine-2-acetamide.
II. 10-Hydroxy-N,5,5-trimethyl-8-(1,2,-dimethylheptyl)-1,2,3,4-tetrahydro-5H-[1]benzopyrano[4,3-c]pyridine-2-acetamide.
III. (8-[5-(4-Fluorophenyl)-2-pentyl])-10-hydroxy-N,5,5-trimethyl-1,2,3,4-tetrahydro-5H-[1]benzopyrano[4,3-c]pyridine-2-acetamide.
IV. 10-Hydroxy-N,N,5,5-tetramethyl-8-(1,2-dimethylheptyl)-1,2,3,4-tetrahydro-5H-[1]benzopyrano[4,3-c]pyridine-2-acetamide.
V. 8-[5-(4-Fluorophenyl)-2-pentyl]-10-hydroxy-N,N,5,5-tetramethyl-1,2,3,4-tetrahydro-5H-[1]benzopyrano[4,3-c] pyridine-2-acetamide.
VI. N-(4-Chlorophenyl)-10-hydroxy-5,5-dimethyl-8-(1,2-dimethylheptyl)-1,2,3,4-tetrahydro-5H-[1]benzopyrano [4,3-c]pyridine-2-acetamide.
VII. 10-Hydroxy-5,5-dimethyl-8-(1,2,-dimethylheptyl)-1,2,3,4-tetrahydro-5H-[1]benzopyrano [4,3-c] pyridine-2-(β-propionamide).
VIII. 8-[5-(4-Fluorophenyl)-2-pentyl]-10-hydroxy-N,N,5,5-tetramethyl-1,2,3,4-tetrahydro-5H-[1] benzopyrano[4,3-c]pyridine-2-(β-propionamide).
IX. 8-[5-(4-chlorophenyl)-2-pentyl]-10-hydroxy-N,5,5-trimethyl-1,2,3,4-tetrahydro-5H-[1] benzopyrano [4,3-c] pyridine-2-acetamide.
X. (8-[5-(4-bromophenyl)-2-pentyl])-10-hydroxy-N,5,5-trimethyl-1,2,3,4-tetrahydro-5H-[1] benzopyrano [4,3-c]pyridine-2-acetamide.
XI. 8-[5-phenyl-2-pentyl])-10-hydroxy-N,5,5-trimethyl-1,2,3,4-tetrahydro-5H-[1] benzopyrano[4,3-c] pyridine-2-acetamide.
XII. 8-[5-(4-methylphenyl)-2-pentyl])-10-hydroxy-N,5,5-trimethyl-1,2,3,4-tetrahydro-5H-[1] benzopyrano [4,3-c] pyridine-2-acetamide.
XIII. Ethyl 10-hydroxy-5,5-dimethyl-8-(1,2-dimethylheptyl)-1,2,3,4-tetrahydro-5H-[1]benzopyrano[4,3-c] pyridine-2-acetate.
XIV. 10-Hydroxy-5,5-dimethyl-8-(1,2-dimethylheptyl)-1,2,3,4-tetrahydro-5H-[1]benzopyrano[4,3-c]pyridine-2-acetic acid.
XV. 10-Hydroxy-5,5-dimethyl-8-(1,2-dimethylheptyl)-N-phenyl-1,2,3,4-tetrahydro-5H-[1]benzopyrano[4,3-c] pyridine-2-acetamide.
XVI. 10-Hydroxy-N,5,5-trimethyl-8-isopropyl-1,2,3,4-tetrahydro-5H-[1]benzopyrano[4,3-c]pyridine-2-acetamide.
XVII. 10-Hydroxy-N,5,5-trimethyl-8-isopropyl-1,2,3,4-tetrahydro-5H-[1]benzopyrano[4,3-c]pyridine-2-acetamide.

The following examples further illustrate the present invention:

EXAMPLE 1

10-Hydroxy-5,5-dimethyl-8-(1,2-Dimethylheptyl)-1,2,3,4-tetrahydro-5H-[1]benzopyrano[4,3-c]pyridine-2-acetamide (IV)

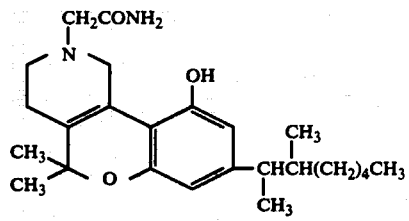

A solution of 1.03 g (0.011 mole) of 2-chloroacetamide in 8 ml of dimethylformamide was added dropwise to a stirred solution of 3.57 g (0.01 mole) of 10-hydroxy-5,5-dimethyl-8-(1,2-dimethylheptyl)-1,2,3,4-tetrahydro-5H- [1] benzopyrano [4,3-c] pyridine in 12 ml of dimethylformamide and 1.11 g (0.011 mole) of triethylamine. After stirring for 17 hours, the mixture was diluted with 20 ml. of water and extracted with ether. The combined ether extracts were washed with water, dried over anhydrous sodium sulfate, and evaporated in vacuo. The residue was recrystallized from acetonitrile, m.p. 165–168°.

Analysis Calculated for $C_{25}H_{38}N_2O_3$: C, 72.42; H, 9.24; N, 6.76

Found: C, 72.29; H, 9.51; N, 6.84.

EXAMPLE 2

10-Hydroxy-N,5,5-trimethyl-8-(1,2-dimethylheptyl)-1,2,3,4-tetrahydro-5H-[1] benzopyrano [4,3-c] pyridine-2-acetamide (V)

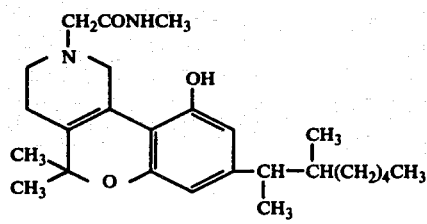

The above titled product was prepared by reacting Compound Ia with 2-chloro-N-methylacetamide according to the method of Example 1. The product was purified by chromatography on a 60–100 mesh Florisil activated magnesium silicate column and graded methanol-chloroform mixtures and recrystallized from acetonitrile; m.p. 131–134°.

Analysis Calculated for $C_{26}H_{40}N_2O_3$: C, 72.86; H, 9.41; N, 6.54

Found: C, 73.12; H, 9.73; N, 6.61

EXAMPLE 3

8-[5-(4-Fluorophenyl)-2-pentyl]-10-hydroxy-N,5,5-trimethyl-1,2,3,4-tetrahydro-5H-[1] benzopyrano[4,3-c]pyridine-2-acetamide (VI)

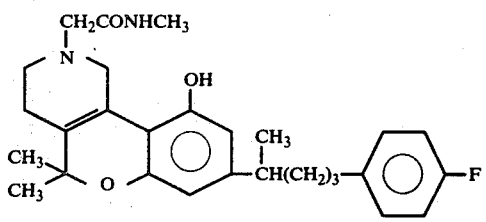

The above titled compound was prepared by reacting 8-[5-(4-fluorophenyl)-2-pentyl]-10-hydroxy-5,5-dimethyl-1,2,3,4-tetrahydro-5H-[1]benzopyrano[4,3-c] pyridine with 2-chlorol-N-methylacetamide as in Example 1. The product was purified by chromatography on a 60–100 mesh Florisil column using graded methanol-chloroform mixtures for development and elution.

Analysis Calculated for $C_{28}H_{35}FN_2O_3$: C, 72.07; H, 7.56; N, 6.01,
Found: C, 71.82; H, 7.69; N, 5.84.

EXAMPLE 4

10-Hydroxy-N,N,5,5-tetramethyl-8-(1,2-dimethylheptyl)-1,2,3,4-tetrahydro-5H-[1]benzopyrano[4,3-c]pyridine-2-acetamide (VII)

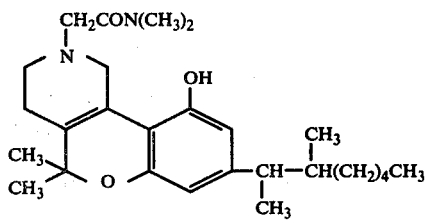

The above-titled compound was prepared by reacting 10-hydroxy-5,5-dimethyl-8-(1,2-dimethylheptyl)-1,2,3,4-tetrahydro-5H-[1]benzopyrano[4,3-c]pyridine with 2-chloro-N,N-dimethylacetamide according to the method of Example 2; m.p. 122–124°.

Analysis Calculated for $C_{27}H_{42}N_2O_3$: C, 73.26; H, 9.57; N, 6.33;
Found C, 73.16; H, 9.75; N, 6.32.

EXAMPLE 5

8-[5-(4-Fluorophenyl)-2-pentyl]-10-hydroxy-N,N,5,5-tetramethyl-1,2,3,4-tetrahydro-5H-[1]benzopyrano[4,3-c]pyridine-2-acetamide (VIII)

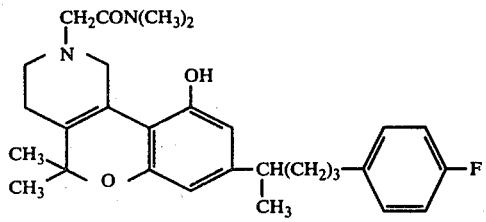

The above-titled compound was prepared by reacting 8-[5-(4-fluorophenyl)-2-pentyl]-10-hydroxy-5,5-dimethyl-1,2, 3,4-tetrahydro-5H-[1]benzopyrano[4,3-c]pyridine with 2-chloro-N,N-dimethylacetamide according to the method of Example 3.

Analysis Calculated for $C_{29}H_{37}FN_2O_3$: C, 72.47; H, 7.76; N, 5.83; Found: C, 72.64; H, 7.94; N, 5.55.

EXAMPLE 6

N-(4-Chlorophenyl)-10-hydroxy-5,5-dimethyl-8-(1,2-dimethylheptyl)-1,2,3,4-tetrahydro-5H-[1]benzopyrano[4,3-c]pyridine-2-acetamide (IX)

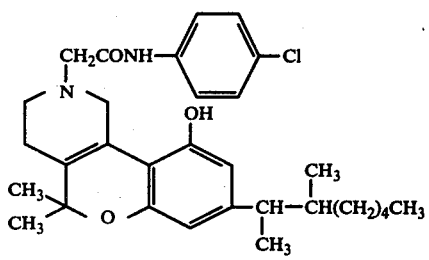

The above-titled compound was prepared by reacting 10-hydroxy-5,5-dimethyl-8-(1,2-dimethylheptyl)-1,2,3,4-tetrahydro-5H-[1] benzopyrano[4,3-c]pyridine with 2-chloro-N-(4-chlorophenyl)acetamide according to the method of Example 1; m.p. 159–160°.

Analysis Calculated for $C_{31}H_{41}ClN_2O_3$: C, 70.90; H, 7.87; N, 5.34; Found: C, 70.90; H, 8.03; N, 5.26

EXAMPLE 7

10-Hydroxy-5,5-dimethyl-8-(1,2-dimethylheptyl)-1,2,3,4-tetrahydro-5H-[1]benzopyrano[4,3-c]pyridine-2-(β-propionamide (X)

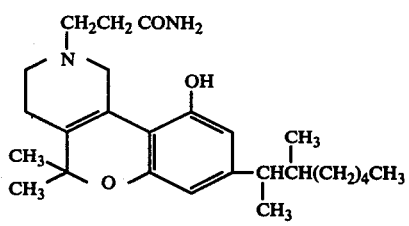

The above titled compound was prepared by reacting 10-hydroxy-5,5-dimethyl-8-(1,2-dimethylheptyl)-1,2,3,4-tetrahydro-5H-[1]benzopyrano[4,3-c]pyridine with 3-chloropropionamide according to the method of Example 2; m.p. 178–180°.

Analysis Calculated for $C_{26}H_{40}N_2O_3$: C, 72.86; H, 9.41; N, 6.53; Found: C, 72.72; H, 9.58; N, 6.43

EXAMPLE 8

8-[5-(4-Fluorophenyl)-2-pentyl]-10-hydroxy-N,N-5,5-tetramethyl-1,2,3,4-tetrahydro-5H-[1]benzopyrano[4,3-c]pyridine-2-(β-propionamide) (XI)

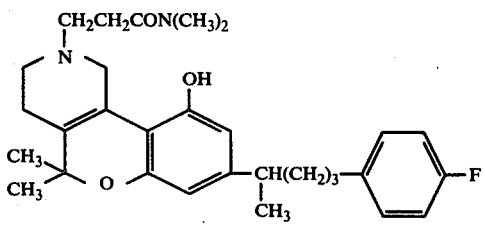

The above-titled compound was prepared by reacting 8-[5-(4-fluorophenyl)-2-pentyl]-10-hydroxy-5,5-dimethyl-1,2,3,4-tetrahydro-5H-[1]benzopyrano[4,3-c]pyridine with 3-chloro-N,N-dimethylpropionamide according to the method of Example 2, m.p. 129–131°.

Analysis Calculated for $C_{30}H_{39}FN_2O_3$: C, 72.84; H, 7.95; N, 5.67; Found: C, 72.80; H, 8.05; N, 5.58

EXAMPLE 9

Ethyl 10-hydroxy-5,5-dimethyl-8-(1,2-dimethylheptyl)-1,2,3,4-tetrahydro-5H-[1]benzopyrano[4,3-c]pyridine-2-acetate (XII)

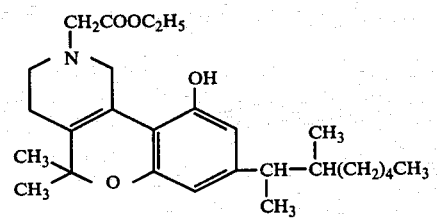

The above-titled compound was prepared by reacting 10-hydroxy-5,5-dimethyl-8-(1,2,-dimethylheptyl)-1,2,3,4-tetrahydro-5H-[1]benzopyrano[4,3-c]pyridine with ethyl bromoacetate according to the method of Example 1. The product was purified by chromatography on a 60–100 mesh Florisil and graded ethanol-chloroform mixtures.

Analysis Calculated for $C_{27}H_{41}NO_4$: C, 73.10; H, 9.32; N, 3.16 Found: C, 72.69; H, 9.51; N, 3.02

EXAMPLE 10

10-Hydroxy-5,5-dimethyl-8-(1,2-dimethylheptyl)-1,2,3,4-tetrahydro-5H-[1]benzopyrano[4,3-c]pyridine-2-acetic acid (XIII)

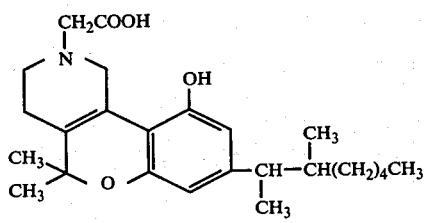

The above-titled compound was obtained by hydrolyzing the product of Example 9 with dilute aqueous sodium hydroxide in methanol; m.p. 192–195°; after recrystallization from ethanol.

EXAMPLE 11

10-Hydroxy-5,5-dimethyl-8-(1,2-dimethylheptyl)-N-phenyl-1,2,3,4-tetrahydro-5H[1]benzopyrano[4,3-c]pyridine-2-acetamide (XIV)

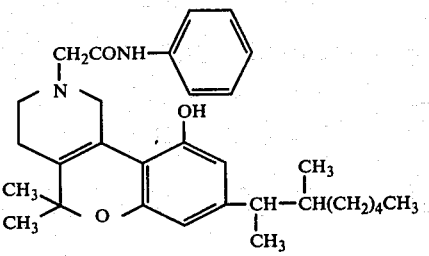

The above-titled compound was prepared by reacting 10-hydroxy-5,5-dimethyl-8-(1,2-dimethylheptyl)-1,2,3,4-tetrahydro-5H-[1]benzopyrano[4,3-c]pyridine with 2-chloro-N-phenylacetamide according to the method of Example 1; m.p. 125–127°.

Analysis Calculated for $C_{31}H_{42}N_2O_3$: C, 75.88; H, 8.63; N, 5.71; Found: C, 76.43; H, 8.88; N, 5.67

EXAMPLE 12

10-Hydroxy-N,5,5-trimethyl-8-isopropyl-1,2,3,4-tetrahydro5H-[1]benzopyrano[4,3-c]pyridine-2-acetamide(XV)

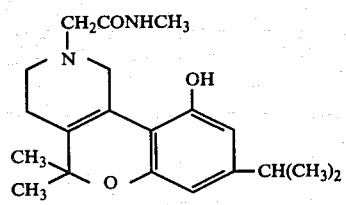

The above-titled compound was prepared by reacting 10-hydroxy-8-isopropyl-5,5-dimethyl-1,2,3,4-tetrahydro-5H-[1]benzopyrano[4,3-c]pyridine with 2-chloro-N-methylacetamide according to the method of Example 1; m.p. 178–190°.

Analysis Calculated for $C_{20}H_{28}N_2O_3$: C, 69.74; H, 8.19; N, 8.13;
Found: C, 69.65; H, 8.30; N, 7.80

EXAMPLE 13

Pharmacological Tests

There were different tests carried out with the present compounds to determine their analgesic and tranquilizing activity. The results for each of the test are set forth below.

TEST I

Rat Desoxyn Antagonism

In this test, the antagonism or potentiation of methamphetamine-induced hyperactivity in rats was evaluated in motor activity chambers equipped with photocells (Lehigh Valley, Model #1497). Groups of rats were premedicated with the test compound and then administered methamphetamine (1 mg/kg., i.p.). One rat was placed in each chamber and three rats were used per test dose. Effect was recorded as percent change, in counts from the photocells compared to methamphetamine-treated controls. In the test results listed in the table below, a plus (+) sign indicates "potentiation", and a minus (−) sign indicates "antagonism". The larger the number, the greater the "potentiation" or the "antagonism".

| Antagonism Effect of Compounds | | |
|---|---|---|
| Compound | Oral Dose, mg./kg. | % Change |
| IV | 20 | −67 |
|  | 80 | −64 |
| V | 20 | −73 |
|  | 80 | −73 |
| VI | 20 | −63 |
|  | 80 | −74 |
| VII | 20 | +36 |
|  | 80 | −26 |
| VIII | 20 | −34 |
|  | 80 | −55 |
| IX | 20 | +43 |
|  | 80 | +38 |
| X | 20 | −18 |
|  | 80 | −13 |
| XI | 20 | +20 |
|  | 80 | +11 |
| XII | 20 | −54 |
|  | 80 | −81 |
| XIV | 20 | −16 |
|  | 80 | +9 |

TEST II

Mouse Writhing Test

In this test, groups of five female mice weighing 18–25 grams were administered the test compound or placebo. In this series of compounds, oral pretreatment was normally one hour. The mice were then injected I.P. with 0.4 ml. of 0.5% acetic acid (v/v). Five minutes after the initial injection for the group, the number of writhes were counted for a twenty minute period. Analgetic activity was expressed as either the percent difference (inhibition) between the number of writhes of the test group and a control vehicle group. The results are listed in the table below. The percentage results indicate a blockade or lessening of writing.

| Effect of Compounds In the Mouse Acetic Acid Writhing Test | | |
|---|---|---|
| Compound | Dose, mg./kg. | % Less Writhes |
| IV | 10 | 6 |
|  | 40 | 82 |
| V | 10 | 66 |
| VI | 10 | 71 |
| VII | 10 | 19 |
|  | 40 | 86 |
| VIII | 10 | 23 |
| IX | 10 | 0 |
| X | 10 | 0 |
| XI | 10 | 6 |
| XIV | 10 | 12 |
| XII | 10 | 35 |
| XV | 10 | 31 |

We claim:

1. A compound of the formula

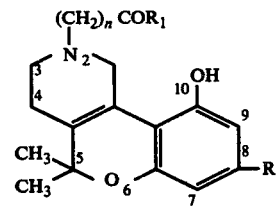

wherein $n = 1$ or 2; R is a $C_3$–$C_{20}$ alkyl, phenylalkyl, halophenylalkyl or loweralkyl phenylalkyl; $R_1$ is $NR_2R_3$ where $R_2$ and $R_3$ each are H, loweralkyl, phenylalkyl, halophenyl alkyl or loweralkyl phenyl.

2. A compound according to claim 1 wherein $n=1$, R is 1,2-dimethylheptyl and $R_1$ is $NH_2$.

3. A compound according to claim 1 wherein $n=1$, R is 1,2-dimethylheptyl and $R_1$ is $NHCH_3$.

4. A compound according to claim 1 wherein $n=1$, R is 4-(4-fluorophenyl)-2-pentyl and $R_1$ is $NHCH_3$.

5. A compound according to claim 1 wherein $n=1$, R is 1,2-dimethylheptyl and $R_1$ is $N(CH_3)_2$.

6. A compound according to claim 1 wherein $n=1$, R is 5-(4-fluorophenyl)-2-pentyl and $R_1$ is $N(CH_3)_2$.

7. A compound according to claim 1 wherein $n=1$, R is 1,2-dimethylheptyl and $R_1$ is

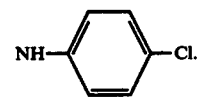

8. A compound according to claim 1 wherein $n=2$, R is 1,2-dimethylheptyl and $R_1$ is $NH_2$.

9. A compound according to claim 1 wherein $n=2$, R is 5-(4-fluorophenyl)-2-pentyl and $R_1$ is $N(CH_3)_2$.

* * * * *